United States Patent

Parthasarathy et al.

(10) Patent No.: US 10,251,610 B2
(45) Date of Patent: Apr. 9, 2019

(54) CONTACT TRACING ANALYTICS

(71) Applicant: International Business Machines Corporation, Armonk, NY (US)

(72) Inventors: Kanagavalli Parthasarathy, Singapore (SG); Saritha S. Pillai, Singapore (SG); Marianne B. Rojo, Singapore (SG); Kishore Sethumadhavan, Singapore (SG); Ronny Syarif, Singapore (SG); Helen Tandiono, Singapore (SG)

(73) Assignee: International Business Machines Corporation, Armonk, NY (US)

(*) Notice: Subject to any disclaimer, the term of this patent is extended or adjusted under 35 U.S.C. 154(b) by 96 days.

(21) Appl. No.: 15/006,214

(22) Filed: Jan. 26, 2016

(65) Prior Publication Data

US 2017/0209102 A1    Jul. 27, 2017

(51) Int. Cl.
| | |
|---|---|
| *G08B 1/08* | (2006.01) |
| *A61B 5/00* | (2006.01) |
| *A61B 5/01* | (2006.01) |
| *G16H 10/60* | (2018.01) |

(52) U.S. Cl.
CPC .......... *A61B 5/7275* (2013.01); *A61B 5/0059* (2013.01); *A61B 5/01* (2013.01); *G16H 10/60* (2018.01); *A61B 2560/0242* (2013.01)

(58) Field of Classification Search
CPC ....... A61B 5/7275; A61B 5/0059; A61B 5/01; A61B 2560/0242; G06F 17/30241; G06F 17/30598; G06F 19/322
USPC .................................................. 340/539.11
See application file for complete search history.

(56) References Cited

U.S. PATENT DOCUMENTS

| | | | |
|---|---|---|---|
| 7,705,723 B2 | 4/2010 | Kahn et al. |
| 8,049,614 B2 | 11/2011 | Kahn et al. |
| 8,405,503 B2 | 3/2013 | Wong |
| 8,645,538 B2 | 2/2014 | Pan |

(Continued)

FOREIGN PATENT DOCUMENTS

| | | |
|---|---|---|
| WO | 2010099488 A1 | 9/2010 |
| WO | 2011005224 A1 | 1/2011 |

OTHER PUBLICATIONS

Fahnrich et al., "Surveillance and Outbreak Response Management System (SORMAS) to support the control of the Ebola virus disease outbreak in West Africa", Submitted Jan. 19, 2015, Published Mar. 26, 2015, 8 pages, <http://www.eurosurveillance.org/ViewArticle.aspx?ArticleId=21071>.

(Continued)

*Primary Examiner* — Naomi J Small
(74) *Attorney, Agent, or Firm* — Alexa L. Ashworth; A. Imtiaz Billah; Andrew Rodionov

(57) ABSTRACT

Contact tracing during an event is provided. Community interaction information for one or more clusters is determined. The community interaction information for a cluster correlates times and physical locations of one or more individuals within an area corresponding to the cluster. It is determined that a first individual has traveled from a first area corresponding to a first cluster to a second area corresponding to a second cluster. The determination is based, at least in part, on correlated times and physical locations of the first individual. One or more at-risk individuals is identified based, at least in part, on the community interaction information of the second cluster.

20 Claims, 5 Drawing Sheets

(56) References Cited

U.S. PATENT DOCUMENTS

| | | | |
|---|---|---|---|
| 2006/0036619 A1 | 2/2006 | Fuerst et al. | |
| 2007/0229290 A1* | 10/2007 | Kahn | G06F 19/00 340/573.4 |
| 2008/0213125 A1* | 9/2008 | Boast | A61L 2/202 422/2 |
| 2008/0318678 A1* | 12/2008 | Stivoric | G06Q 30/0242 463/36 |
| 2009/0265106 A1* | 10/2009 | Bearman | G06Q 10/00 701/300 |
| 2009/0319295 A1* | 12/2009 | Kass-Hout | G06Q 10/1095 705/2 |
| 2010/0256983 A1* | 10/2010 | Perkins | G06Q 10/06 705/2 |
| 2011/0029488 A1* | 2/2011 | Fuerst | G06F 19/3418 707/636 |
| 2013/0031041 A1* | 1/2013 | Maciejewski | G06F 17/18 706/46 |
| 2014/0167917 A2 | 6/2014 | Wallace et al. | |
| 2014/0358573 A1* | 12/2014 | Balinski | G16H 40/63 705/2 |
| 2015/0006192 A1* | 1/2015 | Sudharsan | G06N 5/048 705/2 |
| 2016/0260301 A1* | 9/2016 | Miller | G08B 13/2417 |
| 2017/0024531 A1* | 1/2017 | Malaviya | G06F 19/325 |

OTHER PUBLICATIONS

Leong et al., "Contact Tracing in Healthcare Digital Ecosystems for Infectious Disease Control and Quarantine Management", 2009 3rd IEEE International Conference on Digital Ecosystems and Technologies, Jun. 1-3, 2009, pp. 306-311, IEEE.

\* cited by examiner

CONTACT TRACING ANALYTICS

BACKGROUND OF THE INVENTION

The present invention relates generally to the field of data analysis and more specifically to contact tracing during particular events.

Throughout the course of history, there have been advances in communications and transportation technologies which have greatly influenced individuals at the community, regional and global level. Certain types of events (such as a medical emergency which affects individuals at the community, regional and global level) may inadvertently result from increased interactions among people due to advances in communication and transportation. One of the more effective methods to control such undesirable events is to conduct contact tracing on patients infected with a disease and on the individuals potentially infected.

SUMMARY

According to one embodiment of the present invention, a method for contact tracing during an event is provided, the method comprising: determining, by one or more processors, community interaction information for one or more clusters, wherein the community interaction information for a cluster correlates times and physical locations of one or more individuals within an area corresponding to the cluster; determining, by one or more processors, that a first individual has traveled from a first area corresponding to a first cluster to a second area corresponding to a second cluster, wherein the determination is based, at least in part, on correlated times and physical locations of the first individual; and identifying, by one or more processors, one or more at-risk individuals based, at least in part, on the community interaction information of the second cluster.

According to another embodiment of the present invention, a computer program product for contact tracing during an event is provided. The computer program product comprises a computer readable storage medium and program instructions stored on the computer readable storage medium. The program instructions include: program instructions to determine community interaction information for one or more clusters, wherein the community interaction information for a cluster correlates times and physical locations of one or more individuals within an area corresponding to the cluster; program instructions to determine that a first individual has traveled from a first area corresponding to a first cluster to a second area corresponding to a second cluster, wherein the determination is based, at least in part, on correlated times and physical locations of the first individual; and program instructions to identify one or more at-risk individuals based, at least in part, on the community interaction information of the second cluster.

According to another embodiment of the present invention, a computer system for performing data analysis is provided. The computer system includes one or more computer processors, one or more computer readable storage media, and program instructions stored on the computer readable storage media for execution by at least one of the one or more processors. The program instructions include: program instructions stored on the one or more computer readable storage media for execution by at least one of the one or more processors, the program instructions comprising: program instructions to determine community interaction information for one or more clusters, wherein the community interaction information for a cluster correlates times and physical locations of one or more individuals within an area corresponding to the cluster; program instructions to determine that a first individual has traveled from a first area corresponding to a first cluster to a second area corresponding to a second cluster, wherein the determination is based, at least in part, on correlated times and physical locations of the first individual; program instructions to identify one or more at-risk individuals based, at least in part, on the community interaction information of the second cluster; and program instructions to, in response to determine that the first individual has traveled from the first area to the second area, compile community interaction information associated with the first individual from the first cluster and the second cluster.

DETAILED DESCRIPTION

Figure 1:
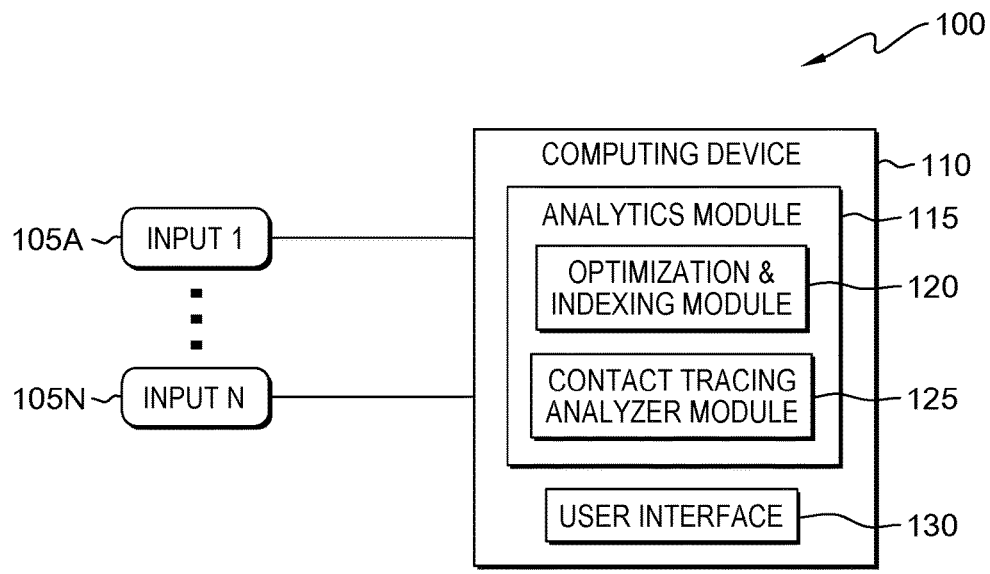
FIG. 1 is a functional block diagram illustrating a data processing environment, generally designated as 100, in accordance with one embodiment of the present invention.

Human beings and other living organisms can be influenced by events of beneficial and deleterious nature. At times, there are deleterious events, such as a medical emergency affecting individuals at the community, regional and global level in the form of the spreading of diseases, which are communicable. As used herein, the term "disease" refers to a disease that is communicable from one individual (e.g., person, animal) to another via any one or more of various transmission vectors (e.g., physical contact between the individuals, infectious microorganism) during a medical emergency. The spreading of a deleterious event at the community, regional, and global level can lead to detrimental health effects (such as infection) and those who have had or continue to have interactions with the infected individuals. One of the ways of stemming the spread of a deleterious event is to investigate and pin-point interactions of those infected with the disease. Embodiments of the present invention provide systems, methods, and computer program products for capturing interaction data which can be collected at locations where the deleterious event has high potential to spread by focusing on interactions at the community, regional, and global level. Additionally, embodiments of the present invention process large amounts of interaction data of multiple individuals by treating the interaction data as discrete data points, processing the discrete data points, and bringing the processed discrete data points together on an as-needed basis.

In some instances, the spread of deleterious events occurs through close interactions between the infected individual and another individual. This is especially true in an enclosed environment such as an office space, school, public transit, etc. Within healthcare facilities such as a doctor's office and a hospital, the situation is aggravated by the infected individual visiting such facilities without knowing that he or she is infected. Due to close proximity with health workers (and the health workers engaging in further interactions with more patients), the deleterious event may spread rapidly.

Thus, embodiments of the present invention recognize a need to obtain information on individuals (e.g., the date, the time, and risk factors with respect to the individual who may be infected—in the context of the present disclosure, this information is community interaction information) who are visiting a facility which is vulnerable to the deleterious event. The need is not as profound to register individuals in spaces which are not as vulnerable to deleterious events with information such as the date, the time, and risk factors with respect to the individual who may be infected. To address privacy concerns in gathering this type of information, analytics module 115 utilizes only information which is properly obtained under applicable laws, rules, and regulations. Analytics module 115 examines data associated with individuals. There is a high volume of data which is available and (at times necessary) to determine at-risk individuals. The sources of data may be disparate and disconnected. These sources of data may include information provided to healthcare workers by individuals connected to an infected individual, social media information that is publicly available or shared by the information owner, or gathered from other systems (e.g., transportation systems).

The present invention will now be described in detail with reference to the Figures. FIG. 1 is a functional block diagram illustrating a data processing environment, generally designated as 100, in accordance with one embodiment of the present invention. FIG. 1 provides only an illustration of implementation and does not imply any limitations with regard to the environments in which different embodiments may be implemented. Modifications to data processing environment 100 may be made by those skilled in the art without departing from the scope of the invention as recited by the claims. In this exemplary embodiment, data processing environment 100 includes inputs 105A-N and computing device 110.

Inputs 105A-N refer to information fed into computing device 110. Inputs 105A-N may derive from a computing system (e.g., a server, a desktop or laptop PC, a PDA or a Smart phone), registration device, images from cameras, etc. The information which is fed into computing device 110 may be a record of interactions an individual has participated in, an individual's body temperature, location, or any type of information relevant to understanding the spreading of a disease within a location. A variable number of inputs may be used in conjunction with analytics module 115 (which is housed within computing device 110).

Inputs 105A-N can be information deriving from a registration device capable of registering a user's information and can measure a user's body temperature quickly. The device may include one or more of: an infrared thermometer to capture the body temperature of the person using the registration device; an input device (e.g., a keyboard for the person using the registration device to type in his or her details); a barcode scanner; a passport reader; a QR code scanner; a screen for the person using the registration device to confirm their input; and the like. The registration device serves as a "data terminal" which has the main function of recording information. This information is sent to a secure central repository (e.g., a cloud computing environment), where it can be accessed as needed. The registration device can be pre-configured to alert healthcare officials that the person currently using the registration device has been exposed to some communicable organism, based on some trigger. These triggers are preconfigured in conjunction with the output "predicted" by the contact tracing algorithm/ model (which is described in more detail with respect to analytics module 115 in FIG. 2). The data set from the registration device may be very large and identifying high risk individuals depends the resources assigned to analytics module 115 and the registration device. The information derived from the registration device can then be used to profile the risk of infection. For example, if the person using the registration device is deemed to have a fever, then he or she is profiled as high risk. The registration device can optionally have an output device such as a ticket receipt which can issue a QR code for the user to do a quick registration at a future point in time, or a sticker generator for the user to generate a "stick-on" indicating that he/she has done registration.

Inputs 105A-N can be information obtained from a data source disparate in nature, format, location, etc. An infrared scanner can be used to measure body temperature and the body temperature information can be stored in a repository to be accessed by analytics module 115. Other information pertaining to a passenger such as countries visited, dates on which the passenger travelled, and future destinations can be obtained and stored in a repository to be accessed by analytics module 115. Image data, such as a photograph, can also be stored in a repository to be accessed by analytics module 115. This information, in text and/or image form, can then be shared between destination points in conjunction with the infrared scanner in order to form a profile of the risk of the group of passengers travelling within an area of interest and/or a mode of transportation.

Inputs 105A-N can be information from digital technologies (i.e., a base two process where digitized information is recorded in binary code of combinations using digits 0 and 1 which represent words and images). Many data points can be derived from digital technologies. Data points which are gathered from (and are not limited to) mobile devices and images from cameras can be used to gain insight into activities performed by individuals and separately assess the risk of further transmission of a medical emergency which affects individuals at the community, regional and global level. Analytics module 115 obtains information from digital technologies pertaining to the location and potential contacts of a potentially infected individual.

Computing device 110 includes user interface 130 and analytics module 115. Computing device 110 may be a laptop computer, a tablet computer, a netbook computer, a personal computer (PC), a desktop computer, a personal digital assistant (PDA), a smart phone, a thin client, or any programmable electronic device capable of communicating with data sources (e.g., inputs 105A-N).

Figure 6:
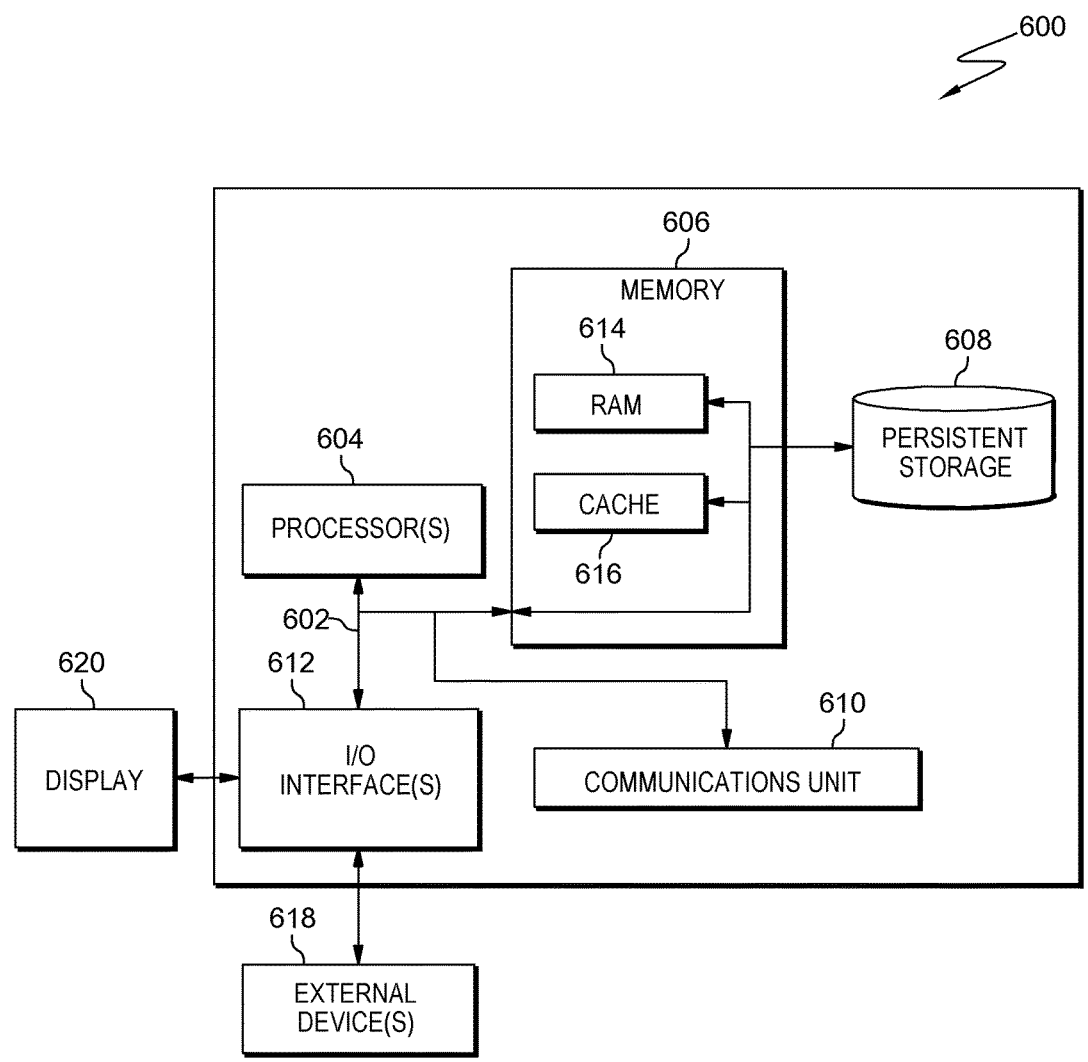
FIG. 6 depicts a block diagram of components of a computing device, in accordance with an illustrative embodiment of the present invention.

Computing device 110 may include internal and external hardware components, as depicted and described in further detail with respect to FIG. 6.

User interface 130 may be a graphical user interface (GUI) or a web user interface (WUI) and can display text, documents, web browser windows, user options, application interfaces, and instructions for operation, and includes the information (such as graphics, text, and sound) a program presents to a user and the control sequences the user employs to control the program. User interface 130 is capable of receiving data, user commands, and data input modifications from a user. User interface 130 is also capable of communicating with analytics module 115.

Analytics module 115 includes optimization & indexing module 120 and contact tracing analyzer module 125. Analytics module 115 collects information from inputs 105A-N in the form of data which is able to get processed in order to track interactions and assess risks of potentially infected individuals. Large amount of interaction data may be processed as discrete data points. After analytics module 115 processes the interaction data, the processed data is mapped and stored within a repository. While investigating the interaction data of potentially infected individuals within a location affected by the deleterious event, analytics program 115 brings up the processed data at a future point on an as-need basis. Thus, efficiency of the analysis time and the breadth of analysis are improved. Further information from inputs 105A-N can be fed to analytics module 115. Analytics module 115 comprises of an algorithm to build a contact tracing output based on certain input parameters (e.g., individuals diagnosed with an infection). In an exemplary embodiment, analytics program 115, using the algorithm, determines other individuals who have had contact with the individuals diagnosed with the infection. Continuing in this embodiment, based on parameters such as the proximity of contact, the method of contact, etc., the algorithm of analytics module 115 builds a list of potentially infected persons. If prior information is available on certain individuals, the algorithm is able to learn from the prior information to build a more accurate model which is able to better form and assess risk profiles. (Analytics program 115 may receive pre-entered information deriving from inputs 105A-N or receive information on an individual pertaining to past events. The reliability of the contact tracing results obtained from analytics program 115 depends on the reliability of the information/data deriving from inputs 105A-N. For example, if the information from inputs 105A-N are outdated, then the contact tracing results are likely unreliable.) Analytics program 115 traces the individuals who might have been exposed to a deleterious event via social contacts, which may impede or stop the spread of a deleterious event. Impeding or stopping the spread of the deleterious event is especially pivotal as individuals can move seamlessly across different borders and boundaries. When there is such dynamic and continuous movement of individuals, interactions become increasingly complex and voluminous. Analytics program 115 applies to the algorithm to store the voluminous amounts of information/data and to analyze the complex nature of the information/data via computer modelling.

Analytics module 115 invokes optimization & indexing module 120 in order to optimize information obtained from inputs 105A-N. The information is initially collected from inputs 105A-N and processed as data to be optimized. Optimization of this data is implemented by grouping data by the time and space where a particular individual (e.g., person who may be identified as someone infected during a deleterious event) has been found. This grouped data is then indexed using the unique identifier for a particular individual. The unique identifier can be information containing a unique national identification number, passport number, and biometric data such as a fingerprint or a facial feature. Body temperature and the unique identifier can be obtained through a registration device or information obtained from transportation facilities (as mentioned above), respectively.

Analytics module 115 invokes contact tracing analyzer module 125 in order to perform contact tracing. Contact tracing is the identification and diagnosis of persons of who have come in contact with an infected person. If it is known that the infected individual has engaged in extensive interactions with others or the infected individual has travelled over a long distance to another discrete location (city, state, country, etc.) via ground, air or sea transportation, then further analysis will potentially be needed to trace the contacts within multiple locations. This type of extensive interaction makes the analysis and the pin-pointing of people who have interacted with the infected individual more involved and complicated. Multiple discrete data points and their interactions with other data points needs to be analyzed. Contact tracing analyzer module 125 takes into account the dynamic nature of these interactions to determine the risk of a potential individual obtaining an infection during an event. The discrete data points may derive from disparate sources of information (i.e., two or more inputs 105A-N) and thus, examining these discrete data points and making determinations (i.e., contact tracing) based on these discrete data points are made more difficult. Analytics module 115 converts all the disparate sources of information into a common format. Analytics module 115 processes information from inputs 105A-N as discrete data points by searching data clusters (see step 420); compiling and organized data from the data clusters (see step 420); filtering out irrelevant data clusters (see step 425); and focusing on relevant data clusters (see step 425). Without performing at least some of these steps, contact tracing of probative value to a user is unlikely. If the data are in different formats, the algorithm of analytics module 115 works in the most optimized manner upon pre-processing the data into a standardized format prior to usage by the algorithm.

Figure 2:
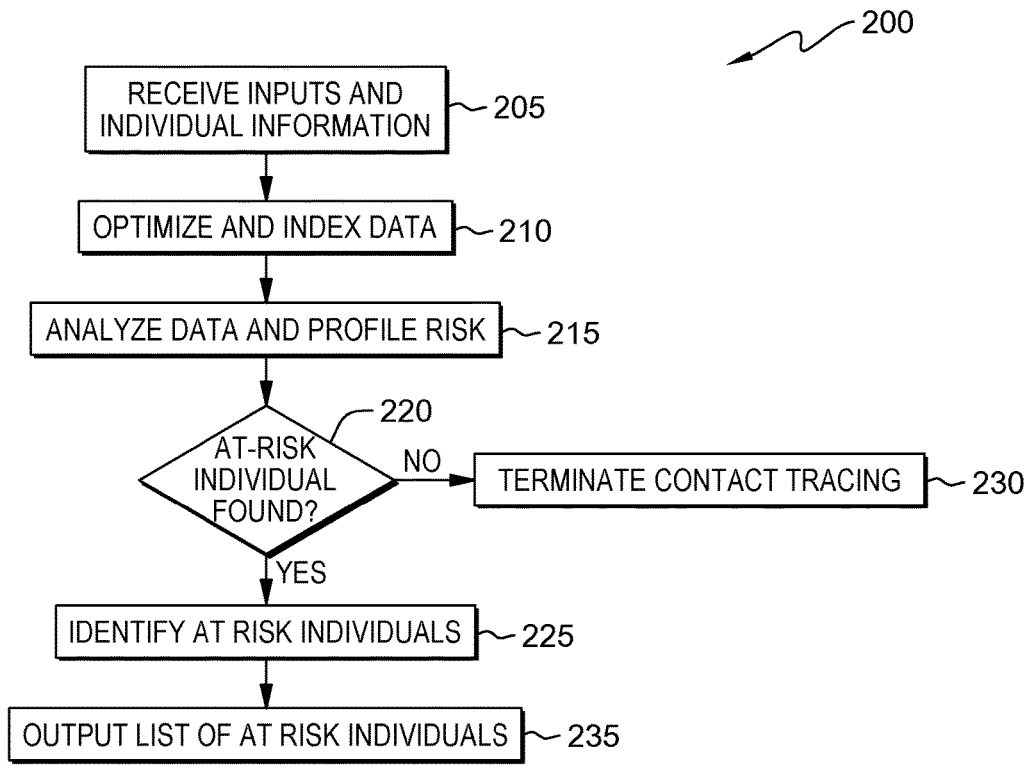
FIG. 2 is a flowchart depicting operational steps, generally designated 200, of the contact tracing performed by analytics module 115, in accordance with an embodiment of the present invention.

FIG. 2 is a flowchart depicting operational steps, generally designated 200, of the contact tracing performed by analytics module 115, in accordance with an embodiment of the present invention.

In step 205, analytics module 115 receives inputs and individual information. The information derived from inputs (i.e., inputs 105A-N) is processed by analytics module 115. Individual information is defined as relevant information pertaining to potential individuals at risk of exposure to infection during a deleterious event and potential individuals infected during a deleterious event. Individual information may include an individual's medical history, travel history, and the like. For example, there is a medical emergency affecting individuals at a regional level which involves the spread of disease O in nation N. Disease O is spread from exposure to handling bush meat (i.e., wild animals hunted for food) and infected bat species. These bat species reside in the swamps of Country X. Epidemiologists investigate certain deleterious events such as a medical emergency which affect individuals at the community, regional and global level. A reasonable starting point in this type of investigation is for analytics module 115 to examine the travel history of the individual infected with disease O. After examining the travel history, analytics module 115 determines that the individual infected with disease O went on a vacation within Country X with a large a population of the species of bats prone to infections of disease O. In this embodiment, the travel history is included in the individual information as relevant information with respect to the individual of interest. Analytics module 115 is able to receive inputs and individual information from inputs 105A-N where the data may be in different formats, and sends the information contained within inputs and individual information to a repository.

In step 210, analytics module 115 optimizes and indexes data. Information derived from inputs 105A-N and the individual information are treated as data to be processed by analytics module 115. The data collected from inputs 105A-N is optimized by grouping the data by a category (e.g., the time and space where a particular individual is). During the deleterious event, this data is then indexed using a unique identifier for a particular individual who is potentially infected. In certain embodiments, inputs 105A-N are disparate in nature and in different data formats. Analytics module 115 examines the data deriving from the disparate nature of inputs 105A-N and applies further analytics to further categorize the data for further processing. The unique identifier can be a unique national identification number, a passport number and biometric data such as a fingerprint or a facial feature. This information can be obtained through a registration device or from a transportation facility (i.e., the examples of inputs 105A-N). The data collected is optimized by taking the information about the individual and returning a subset of information providing where and when the individual potentially infected other individuals. Analytics module 115 works in a loop fashion while processing the optimized and indexed data. Subsequently, analytics module 115 returns any additional information on the other potentially infected individuals due to interactions with an infected individual.

In step 215, analytics module 115 analyzes data and profiles risks. From step 210, analytics module 115 obtains organized data pertaining to individuals who may be at risk of infection. The organized data is optimized, indexed, and analyzed by analytics module 115. In some embodiments, the data was previously in different formats. The organized data is now in a single data format which can be further assessed and permits the comparison of the data associated with one individual with the data associated with another individual. Additional analysis can be done using data from digital technologies via methods such as biometric analysis (e.g., metrics associated with the distinctive and measurable characteristics used to label and describe individuals), mobile device location analysis, etc. In some embodiments, comparisons are made between an unidentified individual who is potentially infected and another individual who is infected using biometric data comparison. Analytics module 115 contains preprocessing capability (i.e., image enhancement) to improve the comparison result. This type of analysis can then be combined and optimized with the data which was previously optimized and indexed information deriving from inputs 105A-N. Data associated with geographic distribution, clinical risk factors, demographics, molecular and phylogenetic features, or sources of exposure such as social networks is evaluated. Analytics module 115 compiles the data and the analysis performed on the data in order to facilitate the integration, synthesis, and visualization of resultant information pertaining to the control, surveillance, and prevention of spreading of the deleterious event. An assessment of resultant information pertaining to the control, surveillance, and prevention of a disease is performed by analytics module 115. This assessment furnishes the profile of individuals at-risk for contracting an infection during a deleterious event at the community, regional, and global level. Analytics module 115 assesses a level of risk for infection. In some embodiments, the level of risk may be "high" or "low."

In step 220, analytics module 115 determines if an at-risk individual risk is found. As stated earlier, the analysis done by analytics module 115 in step 215 yields an assessment of potential individuals at risk of contracting an infection during a deleterious event and potential individuals who have contracted an infection during a deleterious event.

If analytics module 115 determines that a risk is found (decision 220, YES branch), then analytics module 115 identifies at-risk individuals (step 225). The data associated with the identified at risk individuals are stored in a data repository. At later points in time, additional information can be added as an input (to be analyzed) and stored in the data repository.

In step 235, analytics module 115 outputs a list of at risk individuals. The names of the at-risk individuals is provided in the output. Contact information of the at-risk individuals can be presented as an output by configuring the algorithm by which analytics module 115 presents the output. The output presented in step 235 is informationally relevant to contact tracing. The output is kept secure (i.e., confidential) among the users who are working to mitigate the spread of the deleterious event by employing (but not limited to) user account controls and cryptography which are incorporated into analytics module 115.

If analytics module 115 determines that a risk is not found (decision 220, NO branch), then analytics module terminates the contact tracing (step 230). Individuals at-risk are not found in this branch and thus, analytics module 115 terminates the contact tracing (i.e., the cessation of processing the inputs 105A-N and individual information obtained by analytics module 115).

Figure 3:
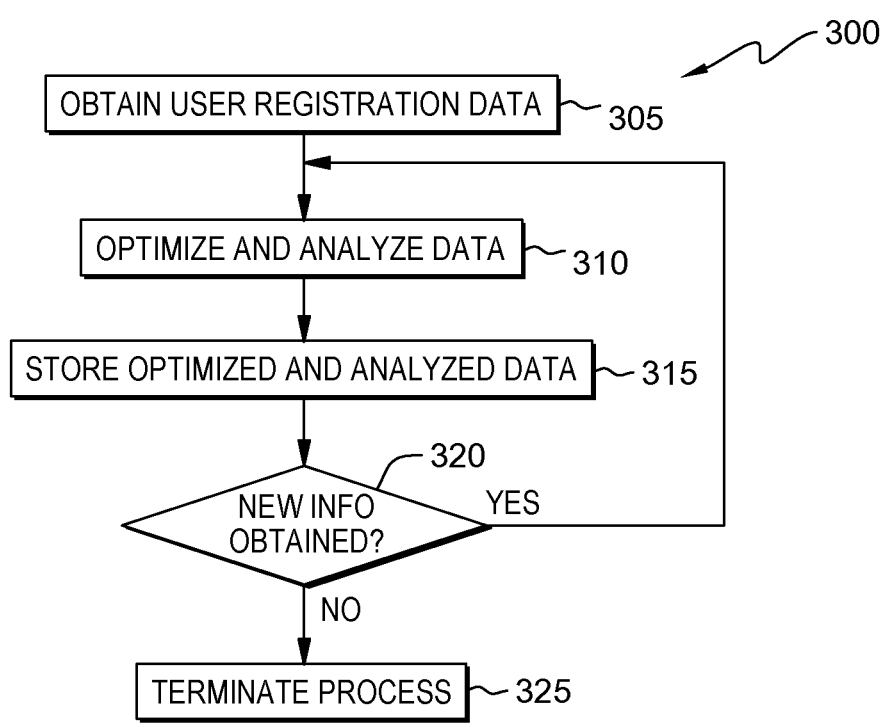
FIG. 3 is a flowchart depicting operational steps, generally designated 300, of the data optimization flow performed by analytics module 115, in accordance with an embodiment of the present invention.

FIG. 3 is a flowchart depicting operational steps, generally designated 300, of the data optimization flow performed by analytics module 115, in accordance with an embodiment of the present invention.

In step 305, analytics module 115 obtains user registration data. The user registration data may derive from input 105A-N (e.g., the registration device, information from healthcare and transportation facilities, and digital technologies). The user registration data is associated with individuals who are investigated for being infected during a deleterious event and individuals at risk for being infected via contact with infected individuals. More specifically, the registration data of an individual comprises body temperature, passport information, biometric data (e.g., a fingerprint or facial feature), a national identification information, medical history, and information pertinent to epidemiology considerations (i.e., patterns, causes, and effects of health conditions in defined populations).

In step 310, analytics module 115 optimizes and analyzes data (from step 305). Step 310 is congruous to steps 210 and 215. Analytics module 115 examines the user registration data from step 305, groups user registration data under a category (e.g., grouping information associated with locations), and indexes user registration data such which is searchable using an identifier. Analytics module 115 analyzes the user registration data in order to yield a risk profile of an individual. More specifically, the registration data is examined by algorithm of analytics module 115 to build a contact tracing output based on interactions of an individual, travel history, and/or other factors which may be of importance during contact tracing. The algorithm builds a model to describe the parameters which influence the risk profile. From the model, risk profiles are assessed to determine if an individual is at risk for infection during a deleterious event and the level of risk of infection for an individual. Also, the data collected from digital technologies may not have a well-defined unique identification. Thus, during optimization, analytics module 115 attempts to map known information from inputs 105A-N through methods such as biometric analysis, mobile location, user registration information, etc.

In step 315, analytics module 115 stores optimized and analyzed data. The stored optimized and analyzed data derives from user registration data. Analytics module 115 houses a repository which stores the optimized and analyzed data. Once the user registration data is optimized, the data can then be stored in a repository and incorporated in shared mapping data for future analysis.

In step 320, analytics module 115 determines if new info is obtained. The analysis performed in step 310 is based on the user registration data obtained in step 305. As new info is obtained and considered in conjunction with user registration data, the risk profile of an individual may change and new risks may be identified.

If in step 320, analytics module 115 determines new info is obtained, then analytics module 115 moves to step 310 (the Yes branch). The new info is optimized and analyzed in conjunction with the user registration data. The risk profile may be altered as a result of this new info. In one exemplary embodiment, individual S travels from the United States to a remote village abroad, RVA. Analysis of the user registration data of S such as his travel history suggests that he is not at risk for disease D within the enclosed area of RVA. RVA is experiencing a medical emergency affecting individuals at the community level in the form of the spread of D. People at risk for D have had exposure to chemicals with aromatic groups. An epidemiologist concerned about D discovers S visited a chemical plant which manufactures the chemicals with aromatic groups on a business trip. This new info is obtained by analytics module 115 and changes the profile risk of S being infected with D. S is now assessed as having a high risk profile for being infected with D.

If in step 320, analytics module 115 determines new info is not obtained, then analytics module 115 moves to step 325 (the No branch). In step 325, analytics module 115 terminates the processes performed by analytics module 115. The information which has analyzed, optimized, and stored has not been altered. Thus, the assessment of this information is not altered. The new info obtained can also be additional identifier data which was previously unknown and can be used for indexing data. For example, analytics module 115 has processed biometric data. Identifier data (e.g., a national identification number or a passport) is newly obtained info. The existing biometric data is eventually matched with the identifier data (e.g., the national identification number or passport). The newly matched information can then also be indexed.

Figure 4:
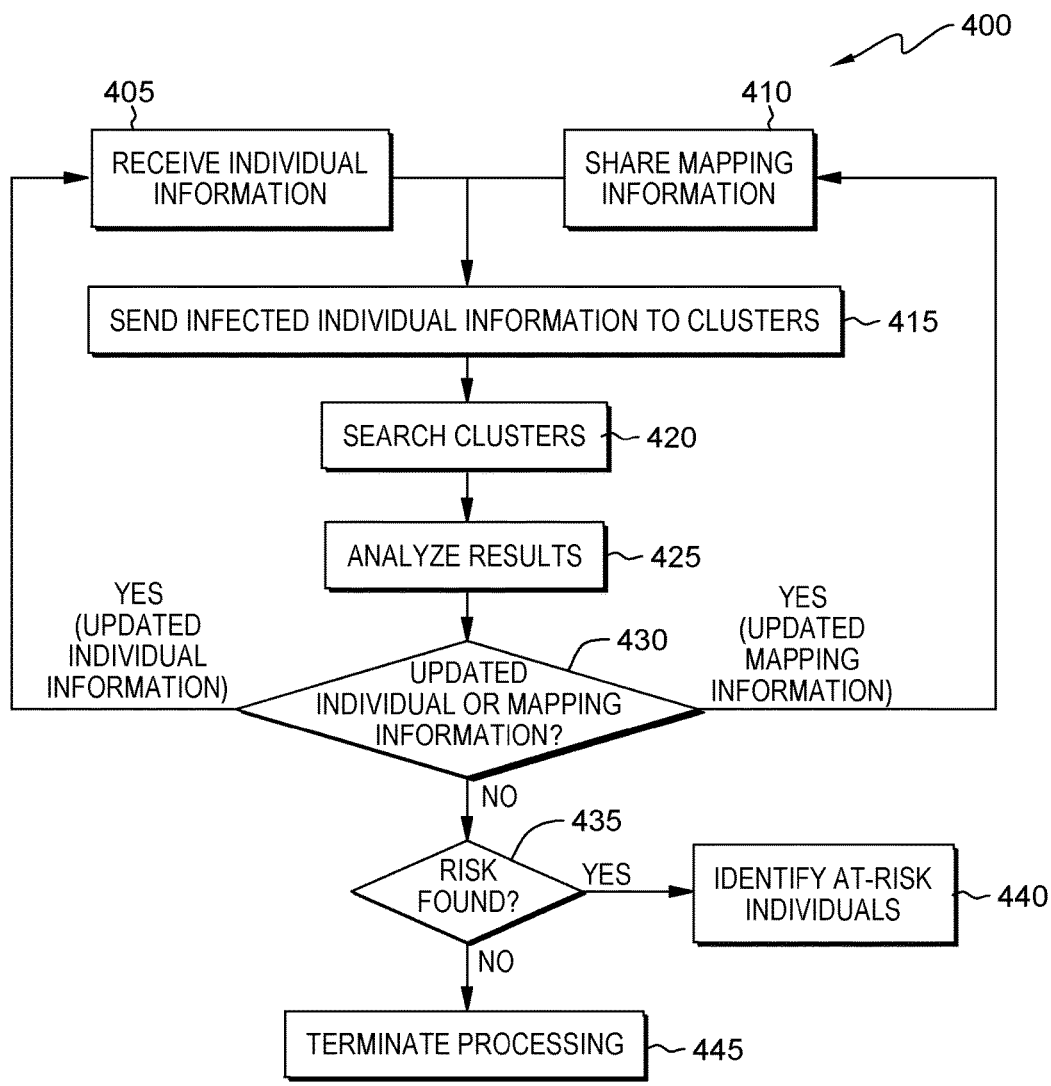
FIG. 4 is a flowchart depicting operational steps, generally designated 400, of the distributed contact tracing performed by analytics module 115, in accordance with an embodiment of the present invention.

FIG. 4 is a flowchart depicting operational steps, generally designated 400, of the distributed contact tracing performed by analytics module 115, in accordance with an embodiment of the present invention.

In step 405, analytics module 115 receives individual information. The individual information can be the body temperature, medical history, travel information, passport information, the user registration information (which is described above), or salient health features (e.g., cuts or bruises) of an individual. This is not an exhaustive list. Depending on the situation and circumstances of a deleterious event, different individual information may be more appropriate. Infected individual information is a type of input utilized by analytics module 115 in order to assess the risk profile of an individual.

In step 410, analytics module 115 shares mapping information. Deleterious events typically occur in enclosed areas. These enclosed areas may or may not contain the individual of interest (who may or may not have the infection). The locales which have experienced the deleterious event are mapped and treated as mapping information. A deleterious event may be further passed on by human contact and the deleterious event is spread within a locale. The mapping human contact network is based on the level of infectiousness, susceptibility of a potential individual, and the diffusion of the disease. Multiple contacts with an infected individual may play a pivotal role in the probability of infection. Analytics module 115 performs contact tracing to map the spread of the infection. In some embodiments, the mapping information comprises nodal points with the aim of pinpointing the interactions of potential individuals believed to be at risk of infection and/or potential individuals with the infection.

In step 415, analytics module 115 sends infected individual information to clusters. Each cluster is a source of discrete information points. A cluster may be a small enclosed area in a distinct location (e.g., data from hospital A and hospital B, data from airport C, etc.). If it is known that the infected individual has had extensive interactions with others, or if the individual has travelled over a long distance to another discrete location (city, state, country, etc.) via ground, air or sea transportation, then analysis is carried out in order to trace the contacts in multiple locations. The multiple locations and interactions are treated as discrete points. Thus, there are multiple discrete points treated as data points which interact with one another to in order to provide a more extensive contact tracing.

In step 420, analytics module 115 searches clusters. This information is securely exposed (through web services, user account controls, cryptography, and other measures which keep data secure and ensure authorized access). The various forms of data can then be compiled in a higher level cluster. (This is created at some logical level such as a city, which will pull and analyze data from various location clusters within the city. Then, a state can have another cluster with data to be collected, analyzed and optimized from various cities, and so forth.). A unique identifier (from step 210) is passed to contact tracing analyzer module 125. The unique identifier is passed to other clusters to find a potentially infected individual. Contact tracing analyzer module 125 analyzes the higher level clusters and extracts information from the various child (i.e., lower level) clusters in order to obtain information on the contact information of the people who are at risk and to provide actionable items which can be fed back to the various clusters as needed. For example, it has been determined that the infected individual has travelled from country A to country C by transiting through country B. The individual has close contact with another person who continued his journey to country D. These interactions and the potential risk will then be analyzed by analytics module 115. The countries A, B, C, and D are treated as clusters and the countries of A, B, C, and D will need to be informed accordingly.

In step 425, analytics module 115 analyzes the results (which are derived from searching through the clusters in step 420, the received infected individual information, and the shared mapping information). If a match for an at-risk candidate is found, analytics module 115 returns information on the potentially infected candidate. At times, the information about which cluster may be influenced by the deleterious event is well established. For example, if the infected individual can provide the places that he/she has visited, then there are established clusters which will be analyzed and optimized. Thus, analytics module 115 performs optimization and analysis by filtering out the "irrelevant" clusters and focusing on the established clusters.

In step 430, analytics module 115 determines if there is updated individual information or updated mapping information. As described in step 320, new information may be obtained after completing the analysis from step 425 of the inputted information from steps 405 and 410. The new information from step 430 may lead to a different assessment after performing the analysis in step 425.

If in step 430, analytics module 115 determines there is updated individual information, then analytics module 115 goes to step 405. At this point, there is new/updated information on the individual and it is entered in as individual information. This updated individual information may or may not influence the assessment made by analytics module 115. Since new information is inputted in, analytics module 115 receives an updated set of individual information. The updated set of individual information is eventually analyzed in conjunction with the shared mapping information and cluster considerations (of steps 415 and 420). For example, the individual of interest may have bruises not noticed before. This new information will be entered into the individual information.

If in step 430, analytics module 115 determines there is updated mapping information, then analytics module 115 goes to step 410. At this point, there is new/updated information on the mapping information. This updated mapping information may or may not influence the assessment made by analytics module 115. Since new information is inputted in, analytics module 115 shares an updated set of mapping information. The updated set of mapping information is eventually analyzed in conjunction with the received individual information and cluster considerations (of steps 415 and 420). For example, the individual of interest was believed to be in close contact with a doctor who treated patients with disease A. However, the doctor who treated patients with disease A has had no human contact for a time period predating this current medical emergency affecting individuals at the global level (i.e., the spreading of A). The "network" from which the mapping information is based on is now different and needs to be updated. The updated "network" will be entered into the mapping information. The updated information may also be additional individual data which was previously unknown and is currently known. Thus, the shared mapping information will be updated as it may further optimize the indexing and analytics algorithm.

If in step 430, analytics module 115 determines there is no updated individual or mapping information, then analytics module goes to step 435. In step 435, analytics module 115 determines if a risk has been found from the analysis performed in step 425.

If in step 435, analytics module 115 determines a risk is found, then analytics module 115 identifies the at risk individuals. The analysis from step 425 yields an assessment and a profile of the risk of individuals who have contracted an infection during the deleterious event and the individuals who may potentially contract an infection during a deleterious event at the community, regional, and global level. The risk (for infection) may be characterized as "high" or "low." The names of the at-risk individuals and a way of contacting these at risk individuals is presented as an output to a user. Information other than a way of contacting at risk individuals can be presented as an output by configuring the algorithm by which analytics module 115 presents the output to the user.

If in step 435, analytics module 115 determines a risk is not found, then analytics module 115 terminates processing. At this point, there is no risk to output and thus there is cessation of processing the inputs 105A-N and individual information obtained by analytics module 115

Figure 5:
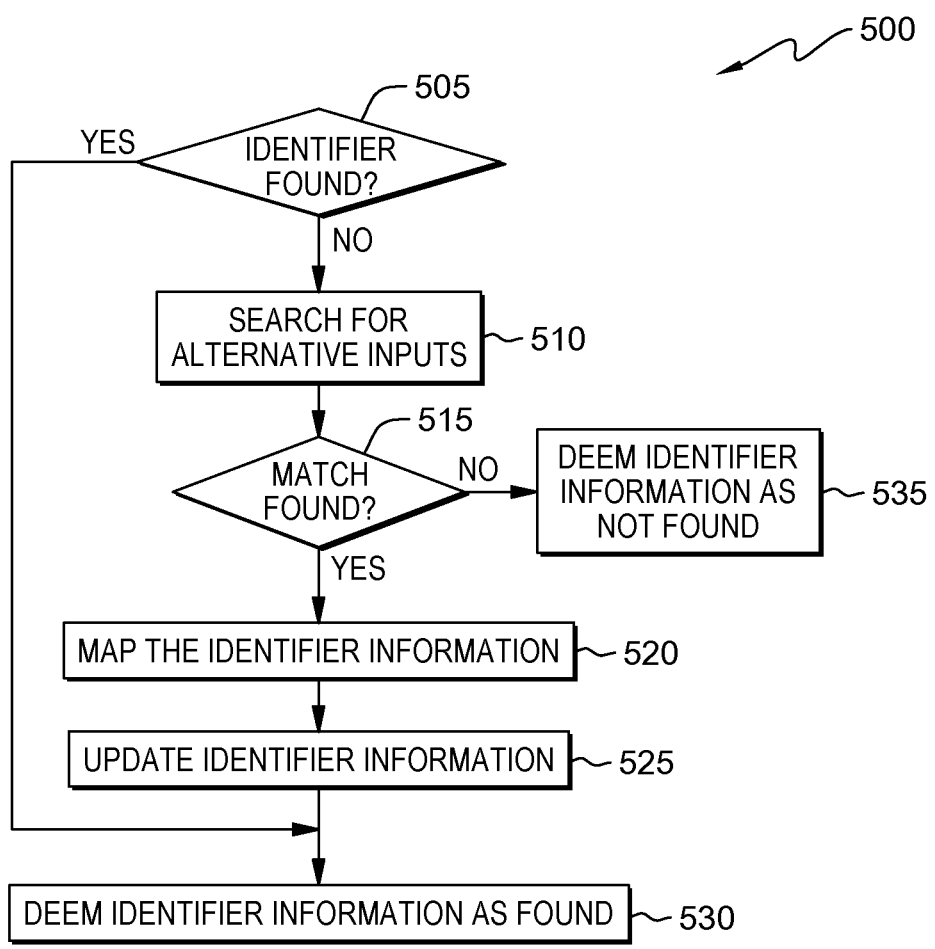
FIG. 5 is a flowchart depicting operational steps, generally designated 500, of identifier matching flow performed by analytics module 115, in accordance with an embodiment of the present invention.

FIG. 5 is a flowchart depicting operational steps, generally designated 500, of identifier matching flow performed by analytics module 115, in accordance with an embodiment of the present invention.

In step 505, analytics module 115 determines if an identifier is found. At a given time, an identifier may or may not be available for an analytics module 115 to be optimized, indexed, and analyzed. At different times, an identifier for the individual may vary. The individual may be identified through his/her national identification number. However when traveling, the unique identifier will be their passport number instead. Additionally, if the data is collected from digital technologies, there may not be a well-defined unique identification.

If in step 505, analytics module 115 determines an identifier is not found, then analytics module 115 searches for alternative inputs in step 510. During optimization performed in steps 210 and 310, analytics module 115 attempts to map information from inputs 105A-N through methods such as biometric analysis, mobile location, user registration information, etc.

In step 515, analytics module 115 determines if a match is found for an identifier. Analytics is performed on the information from inputs 105A-N in order to obtain an identifier which can eventually be mapped by analytics module 115.

If in step 515, analytics module 115 determines a match is found for an identifier, then analytics module 115 maps the identifier information in step 520. The analytics performed on the information from inputs 105A-N is able to obtain an identifier. Once the identifier information is optimized, the data can then be stored in the form of shared mapping data which can be used for future analysis.

In step 515, analytics module 115 determines a match is not found for an identifier, then analytics module 115 deems the identifier information as not found. The analytics performed on the information from inputs 105A-N is unable to obtain an identifier.

In step 525, analytics module 115 updates the identifier information. The inputs as described in steps 405 and 410 is different at step 525, from the inputs in step 405 and 410 at step 505, upon updating the identifier information.

In step 530, analytics module 115 deems the identifier information as found. If in step 505, analytics module 115 determines an identifier has been found, then analytics module 115 deems the information as found.

FIG. 6 depicts a block diagram of components of a computing device, generally designated 600, in accordance with an illustrative embodiment of the present invention. It should be appreciated that FIG. 6 provides only an illustration of one implementation and does not imply any limitations with regard to the environments in which different embodiments may be implemented. Many modifications to the depicted environment may be made.

Computing device 600 includes communications fabric 602, which provides communications between computer processor(s) 604, memory 606, persistent storage 608, communications unit 610, and input/output (I/O) interface(s) 612. Communications fabric 602 can be implemented with any architecture designed for passing data and/or control information between processors (such as microprocessors, communications and network processors, etc.), system memory, peripheral devices, and any other hardware components within a system. For example, communications fabric 602 can be implemented with one or more buses.

Memory 606 and persistent storage 608 are computer readable storage media. In this embodiment, memory 606 includes random access memory (RAM) 614 and cache memory 616. In general, memory 606 can include any suitable volatile or non-volatile computer readable storage media.

Program instructions and data used to practice embodiments of the present invention may be stored in persistent storage 608 for execution and/or access by one or more of the respective computer processors 604 via one or more memories of memory 606. In this embodiment, persistent storage 608 includes a magnetic hard disk drive. Alternatively, or in addition to a magnetic hard disk drive, persistent storage 608 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 608 may also be removable. For example, a removable hard drive may be used for persistent storage 608. Other examples include optical and magnetic disks, thumb drives, and smart cards that are inserted into a drive for transfer onto another computer readable storage medium that is also part of persistent storage 608.

Communications unit 610, in these examples, provides for communications with other data processing systems or devices. In these examples, communications unit 610 includes one or more network interface cards. Communications unit 610 may provide communications through the use of either or both physical and wireless communications links. Program instructions and data used to practice embodiments of the present invention may be downloaded to persistent storage 608 through communications unit 610.

I/O interface(s) 612 allows for input and output of data with other devices that may be connected to computing device 600. For example, I/O interface 612 may provide a connection to external devices 618 such as a keyboard, a keypad, a touch screen, and/or some other suitable input device. External devices 618 can also include portable computer readable storage media such as, for example, thumb drives, portable optical or magnetic disks, and memory cards. Software and data used to practice embodiments of the present invention, e.g., software and data, can be stored on such portable computer readable storage media and can be loaded onto persistent storage 608 via I/O interface(s) 612. I/O interface(s) 612 also connect to a display 620.

Display 620 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience and thus, the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for contact tracing during an event, the method comprising:
    connecting, by one or more processors, a plurality of disparate sources of information to an algorithm, wherein the plurality of disparate sources of information comprise: (i) different data formats containing at least data describing body temperature readings corresponding to a plurality of individuals, data describing a plurality of travel itineraries of destinations traveled with respectively associated traveled dates and times corresponding to each of the plurality of individuals, and data describing a plurality of travel itineraries of destinations scheduled for travel with respectively associated scheduled travel dates and times corresponding to each of the plurality of individuals; and (ii) interaction data which proliferates into a large data set;
    converting, by one or more processors, the plurality of disparate sources of information into a common format amenable for analytics by the algorithm, wherein the algorithm sends the large data set to a data repository;
    determining, by one or more processors, community interaction information for one or more clusters within the common format, wherein the community interaction information for a cluster correlates times and physical locations of one or more individuals within an area corresponding to the cluster;
    performing, by one or more processors, the analytics on the plurality of disparate sources of information converted to the common format, in order to determine that a first individual has traveled from a first area corresponding to a first cluster to a second area corresponding to a second cluster, wherein the determination is based, at least in part, on correlated times and physical locations of the first individual; and
    predicting, by one or more processors, one or more at-risk individuals by generating a list of the one or more at-risk individuals, as contained within the large data set in the data repository, based at least in part on:
        the performed analytics which: (i) account for dynamic events associated with the first cluster and the second cluster, wherein the dynamic events include a plurality of seamless interactions within the first cluster and the second cluster and between the first cluster and the second cluster, and (ii) derive discrete data from the plurality of disparate sources of information,
        the community interaction information of the second cluster,
        the data describing the plurality of travel itineraries of destinations traveled with respectively associated traveled dates and times corresponding to each of the at-risk individuals among the plurality of individuals, and
        the data describing the plurality of travel itineraries of destinations scheduled for travel with respectively associated scheduled travel dates and times corresponding to each of the at-risk individuals among the plurality of individuals.

2. The method of claim 1, wherein determining the community interaction information for the one or more clusters further comprises:
    obtaining, by one or more processors, medical information associated with the one or more individuals within the area of the one or more clusters, wherein the obtained medical information may be modified based on the performed analytics; and
    obtaining, by one or more processors, risk information associated with the area to which the one or more clusters correspond to, wherein the obtained risk information may be modified based on the performed analytics.

3. The method of claim 2, wherein obtaining medical information associated with the one or more individuals comprises:
    obtaining, by one or more processors, patient information from a registration device containing an infrared scanner, wherein the patient information includes body temperatures determined by the infrared scanner for the one or more individuals; and
    obtaining, by one or more processors, information associated with the one or more individuals via one or more environmental sensors including at least a mobile communications device and an imaging device.

4. The method of claim 1, wherein performing the analytics on the disparate sources of information, comprises:
   optimizing, by one or more processors, the community interaction information for the one or more clusters by grouping data within a defined category wherein disparate sources of the community interaction information are converted into a common data format for further optimization, newly acquired information is received, a first set of the community interaction information is excluded from further optimization, and a second set of the community interaction information is included for further optimization;
   indexing, by one or more processors, the data within the defined category utilizing an identifier for at least one individual wherein the optimized data is contained within the identifier, the identifier is searchable, and newly acquired information is received;
   creating, by one or more processors, a profile based on the optimized and indexed data within the defined category; and
   identifying, by one or more processors, the one or more at-risk individuals based, at least in part, on the profile and the optimized and indexed data.

5. The method of claim 1, further comprising:
   in response to determining that the first individual has traveled from the first area to the second area, compiling, by one or more processors, community interaction information associated with the first individual from the first cluster and the second cluster.

6. The method of claim 1, wherein identifying the one or more at-risk individuals further comprises:
   performing, by one or more processors, contact tracing at different cluster levels; and
   extracting, by one or more processors, data from different cluster levels to obtain contact information of the one or more at-risk individuals.

7. The method of claim 6, further comprising:
   providing, by one or more processors, to a user at least one name or contact information for at least one of the one or more at-risk individuals.

8. A computer program product for contact tracing during an event, the computer program product comprising:
   a computer readable storage medium and program instructions stored on the computer readable storage medium, the program instructions comprising:
   program instructions to connect a plurality of disparate sources of information to an algorithm, wherein the plurality of disparate sources of information comprise: (i) different data formats containing at least data describing body temperature readings corresponding to a plurality of individuals, data describing a plurality of travel itineraries of destinations traveled with respectively associated traveled dates and times corresponding to each of the plurality of individuals, and data describing a plurality of travel itineraries of destinations scheduled for travel with respectively associated scheduled travel dates and times corresponding to each of the plurality of individuals; and (ii) interaction data which proliferates into a large data set;
   program instructions to convert the plurality of disparate sources of information into a common format amenable for analytics by the algorithm, wherein the algorithm stores the large data set, wherein the algorithm sends the large data set to a data repository;
   program instructions to determine community interaction information for one or more clusters within the common format, wherein the community interaction information for a cluster correlates times and physical locations of one or more individuals within an area corresponding to the cluster;
   program instructions to perform analytics on the plurality of disparate sources of information converted to the common format, in order to determine that a first individual has traveled from a first area corresponding to a first cluster to a second area corresponding to a second cluster, wherein the determination is based, at least in part, on correlated times and physical locations of the first individual; and
   program instructions to predict one or more at-risk individuals by generating a list of the one or more at-risk individuals, as contained within the large data set in the data repository, based at least in part on:
      the performed analytics which: (i) account for dynamic events associated with the first cluster and the second cluster, wherein the dynamic events include a plurality of seamless interactions within the first cluster and the second cluster and between the first cluster and the second cluster, and (ii) derive discrete data from the plurality of disparate sources of information,
      the community interaction information of the second cluster;
      the data describing the plurality of travel itineraries of destinations traveled with respectively associated traveled dates and times corresponding to each of the at-risk individuals among the plurality of individuals, and
      the data describing the plurality of travel itineraries of destinations scheduled for travel with respectively associated scheduled travel dates and times corresponding to each of the at-risk individuals among the plurality of individuals.

9. The computer program product of claim 8, wherein the program instructions to determine the community interaction information for the one or more clusters further comprise:
   program instructions to obtain medical information associated with the one or more individuals within the area of the one or more clusters, wherein the obtained medical information may be modified based on the performed analytics; and
   program instructions to obtain risk information associated with the area to which the one or more clusters correspond to, wherein the obtained risk information may be modified based on the performed analytics.

10. The computer program product of claim 9, wherein the program instructions to obtaining medical information associated with the one or more individuals, comprise:
   program instructions to obtain patient information from a registration device containing an infrared scanner, wherein the patient information includes body temperatures determined by the infrared scanner for the one or more individuals; and
   program instructions to obtain information associated with the one or more individuals via one or more environmental sensors including at least a mobile communications device and an imaging device.

11. The computer program product of claim 8, wherein program instructions to perform the analytics on the disparate sources of information, further comprise:

program instructions to optimize the community interaction information for the one or more clusters by grouping data within a defined category wherein disparate sources of the community interaction information are converted into a common data format for further optimization, newly acquired information is received, a first set of the community interaction information is excluded from further optimization, and a second set of the community interaction information is included for further optimization;

program instructions to index the data within the defined category utilizing an identifier for at least one individual wherein the optimized data is contained within the identifier, the identifier is searchable, and newly acquired information is received;

program instructions to create a profile based on the optimized and indexed data within the defined category; and program instructions to identify the one or more at-risk individuals based, at least in part, on the profile and the optimized and indexed data.

12. The computer program product of claim 8, wherein the program instructions further comprise:

program instructions to, in response to determining that the first individual has traveled from the first area to the second area, compile community interaction information associated with the first individual from the first cluster and the second cluster.

13. The computer program product of claim 8, wherein the program instructions to identify the one or more at-risk individuals further comprise:

program instructions to perform contact tracing at different cluster levels; and program instructions to extract data from different cluster levels to obtain contact information of the one or more at-risk individuals.

14. The computer program product of claim 13, wherein the program instructions further comprise:

program instructions to provide to a user at least one name or contact information for at least one of the one or more at-risk individuals.

15. A computer system for contact tracing during an event, the computer system comprising:

one or more computer processors;

one or more computer readable storage media;

program instructions stored on the one or more computer readable storage media for execution by at least one of the one or more processors, the program instructions comprising:

program instructions to connect a plurality of disparate sources of information to an algorithm, wherein the plurality of disparate sources of information comprise: (i) different data formats containing at least data describing body temperature readings corresponding to a plurality of individuals, data describing a plurality of travel itineraries of destinations traveled with respectively associated traveled dates and times corresponding to each of the plurality of individuals, and data describing a plurality of travel itineraries of destinations scheduled for travel with respectively associated scheduled travel dates and times corresponding to each of the plurality of individuals; and (ii) interaction data which proliferates into a large data set;

program instructions to convert the plurality of disparate sources of information into a common format amenable for analytics by the algorithm, wherein the algorithm stores the large data set, wherein the algorithm sends the large data set to a data repository;

program instructions to determine community interaction information for one or more clusters within the common format, wherein the community interaction information for a cluster correlates times and physical locations of one or more individuals within an area corresponding to the cluster;

program instructions to perform analytics on the plurality of disparate sources of information converted to the common format, in order to determine that a first individual has traveled from a first area corresponding to a first cluster to a second area corresponding to a second cluster, wherein the determination is based, at least in part, on correlated times and physical locations of the first individual; and program instructions to predict one or more at-risk individuals by generating a list of the one or more at-risk individuals, as contained within the large data set in the data repository, based at least in part on:

the performed analytics which: (i) account for dynamic events associated with the first cluster and the second cluster, wherein the dynamic events include a plurality of seamless interactions within the first cluster and the second cluster and between the first cluster and the second cluster, and (ii) derive discrete data from the plurality of disparate sources of information, the community interaction information of the second cluster;

the data describing the plurality of travel itineraries of destinations traveled with respectively associated traveled dates and times corresponding to each of the at-risk individuals among the plurality of individuals, and the data describing the plurality of travel itineraries of destinations scheduled for travel with respectively associated scheduled travel dates and times corresponding to each of the at-risk individuals among the plurality of individuals.

16. The computer system of claim 15, wherein the program instructions to determine the community interaction information for the one or more clusters further comprise:

program instructions to obtain medical information associated with the one or more individuals within the area of the one or more clusters, wherein the obtained medical information may be modified based on the performed analytics; and program instructions to obtain risk information associated with the area to which the one or more clusters correspond to, wherein the obtained risk information may be modified based on the performed analytics.

17. The computer system of claim 16, wherein the program instructions to obtain medical information associated with the one or more individuals, comprise:

program instructions to obtain patient information from a registration device, wherein the patient information includes body temperatures of the one or more individuals; and program instructions to obtain information associated with the one or more individuals via one or more environmental sensors including at least a mobile communications device and an imaging device.

18. The computer system of claim 15, wherein program instructions to perform the analytics on the disparate sources of information, further comprise:

program instructions to optimize the community interaction information for the one or more clusters by grouping data within a defined category wherein disparate sources of the community interaction information are converted into a common data format for further optimization, newly acquired information is received, a first set of the community interaction information is excluded from further optimization, and a second set of the community interaction information is included for further optimization;

program instructions to index the data within the defined category utilizing an identifier for at least one individual wherein the optimized data is contained within the identifier, the identifier is searchable, and newly acquired information is received;

program instructions to create a profile based on the optimized and indexed data within the defined category; and program instructions to identify the one or more at-risk individuals based, at least in part, on the profile and the optimized and indexed data.

19. The computer system of claim 15, wherein the program instructions to identify the one or more at-risk individuals further comprise:

program instructions to perform contact tracing at different cluster levels; and program instructions to extract data from different cluster levels to obtain contact information of the one or more at-risk individuals.

20. The computer system of claim 19, wherein the program instructions further comprise:

program instructions to provide to a user at least one name or contact information for at least one of the one or more at-risk individuals.

* * * * *